United States Patent
Yoshimi et al.

(10) Patent No.: US 7,834,322 B2
(45) Date of Patent: Nov. 16, 2010

(54) RADIATION IMAGE CAPTURING SYSTEM

(75) Inventors: Takuya Yoshimi, Yokohama (JP); Eiichi Kito, Minami-ashigara (JP); Tsuyoshi Tanabe, Odawara (JP); Takeshi Kuwabara, Minami-ashigara (JP); Kazuhara Ueta, Suginami-ku (JP); Makoto Iriuchijima, Ora-gun (JP); Yasunori Ohta, Yokohama (JP)

(73) Assignee: FUJIFILM Corporation, Tokyo (JP)

( * ) Notice: Subject to any disclaimer, the term of this patent is extended or adjusted under 35 U.S.C. 154(b) by 10 days.

(21) Appl. No.: 12/180,199

(22) Filed: Jul. 25, 2008

(65) Prior Publication Data
US 2009/0026392 A1    Jan. 29, 2009

(30) Foreign Application Priority Data
Jul. 27, 2007  (JP) ............................ 2007-195368
Jun. 26, 2008  (JP) ............................ 2008-167096

(51) Int. Cl.
*H01L 27/146*    (2006.01)
(52) U.S. Cl. ............................................ 250/370.09
(58) Field of Classification Search ............. 250/370.09
See application file for complete search history.

(56) References Cited

U.S. PATENT DOCUMENTS

| 7,528,376 B2* | 5/2009 | Shoji ..................... 250/370.09 |
| 2005/0205813 A1* | 9/2005 | Ishikawa .................... 250/584 |
| 2006/0169907 A1* | 8/2006 | Shinden ................. 250/370.09 |
| 2007/0229287 A1* | 10/2007 | Morgan .................. 340/573.1 |

FOREIGN PATENT DOCUMENTS

| JP | 2000-105297 A | 4/2000 |
| JP | 2003-172783 A | 6/2003 |
| JP | 3494683 B2 | 11/2003 |
| JP | 2005-245828 A | 9/2005 |

* cited by examiner

*Primary Examiner*—David P Porta
*Assistant Examiner*—Mindy Vu
(74) *Attorney, Agent, or Firm*—Sughrue Mion, PLLC

(57) ABSTRACT

A transceiver of a radiation detecting cassette receives subject ID information from an RFID tag by way of wireless communications. An ID checker checks the subject ID information received by the transceiver against a plurality of subject ID information stored in an RFID memory. If the subject ID information received by the transceiver matches one of the subject ID information stored in the RFID memory, then the ID checker associates the matching subject ID information with a radiation dose that is stored in a dose storage unit and corresponds to the matching subject ID information.

14 Claims, 8 Drawing Sheets

RADIATION IMAGE CAPTURING SYSTEM

BACKGROUND OF THE INVENTION

1. Field of the Invention

The present invention relates to a radiation image capturing system including a radiation detecting cassette housing therein a radiation conversion panel for detecting a radiation that has passed through a subject and converting the detected radiation into radiation image information.

2. Description of the Related Art

In the medical field, there have widely been used radiation image capturing apparatus which apply a radiation to a subject and guide the radiation that has passed through the subject to a radiation conversion panel, which captures a radiation image from the radiation. Known forms of the radiation conversion panel include a conventional radiation film for recording a radiation image by way of exposure, and a stimulable phosphor panel for storing a radiation energy representing a radiation image in a phosphor and reproducing the radiation image as stimulated light by applying stimulating light to the phosphor. The radiation film with the recorded radiation image is supplied to a developing device to develop the radiation image, or the stimulable phosphor panel is supplied to a reading device in order to read the radiation image as a visible image.

In the operating room or the like, it is necessary to read recorded radiation images immediately from the radiation conversion panel after the radiation image has been captured, for the purpose of quickly and appropriately treating the patient. As a radiation conversion panel that meets such a requirement, there has been developed a radiation detector having a solid-state detector for converting radiation directly into electric signals or for converting radiation into visible light with a scintillator and then converting the visible light into electric signals, so as to read the detected radiation image.

Radiation image capturing systems which incorporate a radiation detecting cassette housing such a radiation conversion panel therein employ subject ID information for identifying a patient as a subject to capture a radiation image and manage radiation image information (see Japanese Laid-Open Patent Publication No. 2003-172783 and Japanese Laid-Open Patent Publication No. 2005-245828).

Specifically, Japanese Laid-Open Patent Publication No. 2003-172783 discloses that identification information about the capture of radiation images including subject ID information is stored in advance in a memory in a radiation detecting cassette, and each time a radiation image is captured, the identification information about a next subject to be imaged is displayed on a display device for efficiently capturing the radiation images of the subjects.

Japanese Laid-Open Patent Publication No. 2005-245828 discloses that subject ID information on an ID tag applied to a portion of the body of a patient is read by a portable medical terminal and transmitted to a medical facility computer.

The dose of a radiation that is applied from a radiation source through a subject to a radiation detecting cassette for capturing a radiation image of the subject differs from subject to subject. Specifically, since each subject needs to be irradiated with an optimum radiation dose for the subject, the radiation dose has to be managed or adjusted for each patient. According to Japanese Laid-Open Patent Publication No. 2003-172783 and Japanese Laid-Open Patent Publication No. 2005-245828, however, as the radiation dose is not managed or adjusted for each patient, each patient cannot be irradiated with an optimum radiation dose for the subject when capturing the radiation image of the patient.

SUMMARY OF THE INVENTION

It is an object of the present invention to provide a radiation image capturing system which is capable of managing and adjusting the dose of a radiation to be applied to a patient for each of the patients whose radiation images need to be captured.

A radiation image capturing system according to the present invention includes a radiation source for outputting a radiation, a radiation detecting cassette housing therein a radiation conversion panel for detecting a radiation that has passed through a subject and converting the detected radiation into radiation image information, an RFID tag mounted on the subject and storing subject ID information for identifying the subject, an ID storage unit for storing a plurality of pieces of subject ID information, an ID checker, a radiation dose storage unit for storing radiation doses corresponding to the subject ID information, the radiation detecting cassette comprising a first wireless communication unit, and an image capturing apparatus having a second wireless communication unit for performing wireless communications with the first wireless communication unit, the radiation source being disposed in the image capturing apparatus, wherein the first wireless communication unit receives the subject ID information from the RFID tag by way of wireless communications, and wherein the ID checker checks the subject ID information received by the first wireless communication unit against the subject ID information stored in the ID storage unit, and if the subject ID information received by the first wireless communication unit matches one of the subject ID information stored in the ID storage unit, the ID checker associates the matching subject ID information with a radiation dose which is stored in the radiation dose storage unit and which corresponds to the matching subject ID information.

According to the present invention, the first wireless communication unit receives the subject ID information from the RFID tag by way of wireless communications, and the ID checker checks the received subject ID information against the subject ID information stored in the ID storage unit. If the received subject ID information matches one of the subject ID information stored in the ID storage unit, then the ID checker associates the matching subject ID information with a radiation dose which is stored in the radiation dose storage unit and corresponds to the matching subject ID information.

The radiation dose can thus be managed for each patient, and hence the radiation dose of the radiation to be applied to the patient whose radiation image is to be captured can be adjusted for each patient.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
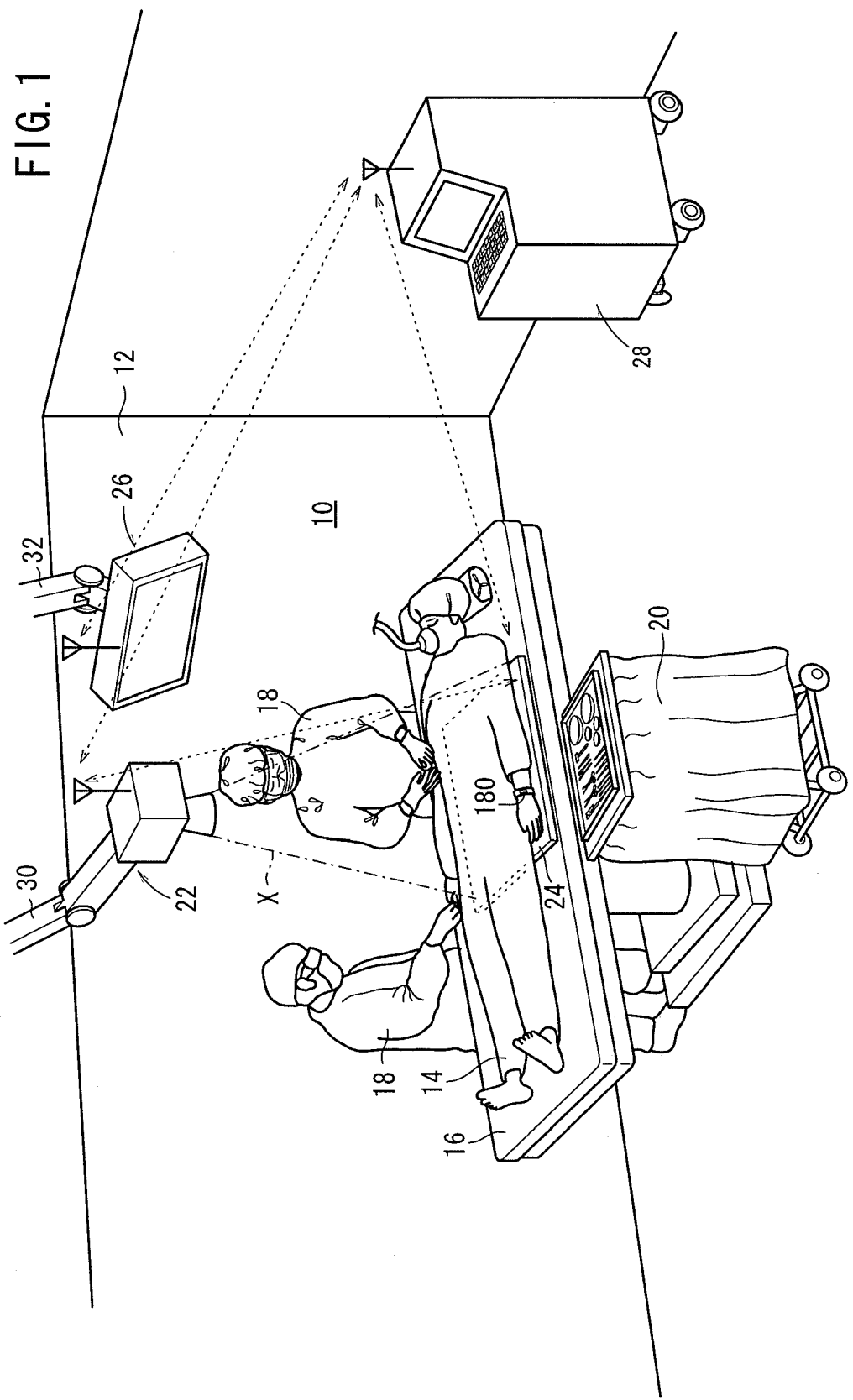
FIG. 1 is a perspective view of an operating room incorporating a radiation image capturing system according to an embodiment of the present invention.

As shown in FIG. 1, an operating room 12 incorporating a radiation image capturing system 10 according to a preferred embodiment of the present invention has a surgical table (bed) 16 for a patient 14 to lie thereon, and an instrument table 20 disposed on one side of the surgical table 16 for placing thereon various tools and instruments to be used by surgeons 18 operating on the patient 14. The surgical table 16 is surrounded by various apparatus required for performing surgical operations, including an anesthesia apparatus, an aspirator, an electrocardiograph, a blood pressure monitor, etc.

The radiation image capturing system 10 includes an image capturing apparatus 22 for irradiating the patient 14 as a subject with radiation X at a dose (radiation dose) according to image capturing conditions, a radiation detecting cassette 24 housing therein a radiation detector (radiation conversion panel) 40 (see FIGS. 2 through 5) for detecting radiation X that has passed through the patient 14, a display device 26 for displaying a radiation image based on radiation X that is detected by the radiation detector 40, and a console (controller) 28 for controlling the image capturing apparatus 22, the radiation detecting cassette 24, and the display device 26. A wrist band 180 having an RFID (Radio Frequency IDentification) tag 182 storing therein subject ID information for identifying the patient 14 is mounted on a wrist of the patient 14 (see FIGS. 1 and 3). The image capturing apparatus 22, the radiation detecting cassette 24, the display device 26, and the console 28 send and receive signals by way of UWB (Ultra-Wide Band) wireless communications. The radiation detecting cassette 24 and the RFID tag 182 also send and receive signals by way of UWB wireless communications.

The image capturing apparatus 22 is coupled to a universal arm 30 so as to be movable to a desired position for capturing images at a desired area of the patient 14, and also to be retractable to an out-of-the-way position while the surgeons 18 are performing a surgical operation on the patient 14. Similarly, the display device 26 is coupled to a universal arm 32, so as to be movable to a position where the surgeons 18 can easily confirm the captured radiation image, which is displayed on the display device 26.

Figure 2:
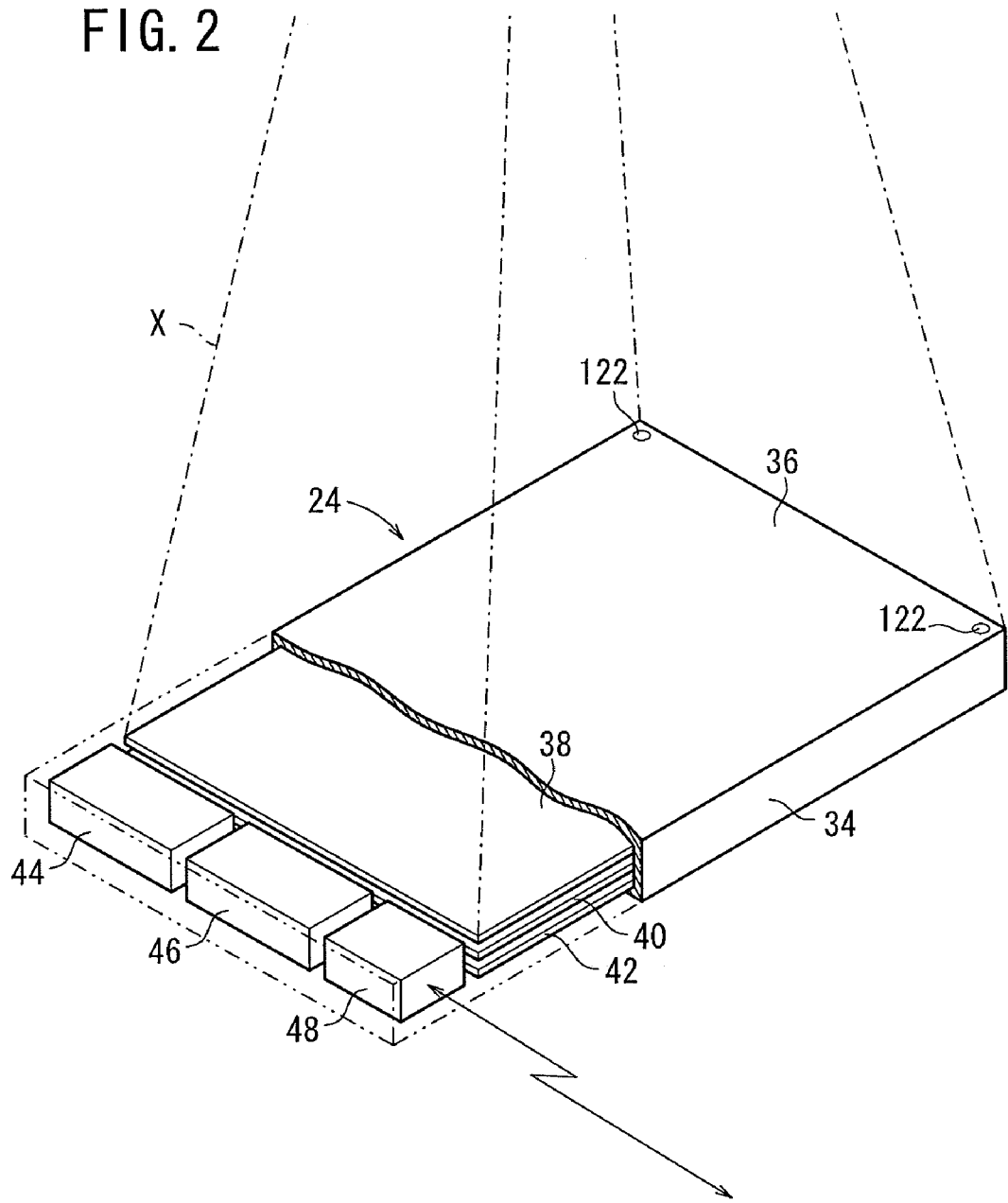
FIG. 2 is a perspective view, partly cut away, showing internal structural details of a radiation detecting cassette used in the radiation image capturing system shown in FIG. 1.

FIG. 2 shows in perspective the internal structural details of the radiation detecting cassette 24. As shown in FIG. 2, the radiation detecting cassette 24 has a casing 34 made of a material that is permeable to radiation X. The casing 34 houses therein a grid 38 for removing scattered rays from the radiation X from the patient 14, a radiation detector 40 for detecting radiation X that has passed through the patient 14, and a lead plate 42 for absorbing back scattered rays from the radiation X. The grid 38, the radiation detector 40, and the lead plate 42 are successively arranged in that order from an irradiated surface 36 of the casing 34, which is irradiated with radiation X. The irradiated surface 36 of the casing 34 may also be constructed so as to form the grid 38.

The casing 34 also houses therein a battery 44, which makes up a power supply for the radiation detecting cassette 24, a cassette controller 46 for energizing the radiation detector 40 with electric power supplied from the battery 44, and a transceiver (first wireless communication unit) 48 for sending and receiving signals including information of the radiation X that is detected by the radiation detector 40, to and from the console 28. A shield plate of lead or the like should preferably be placed over the side surfaces of the cassette controller 46 and the transceiver 48 under the irradiated surface 36 of the casing 34, so as to protect the cassette controller 46 and the transceiver 48 against damage, which would otherwise be caused if the cassette controller 46 and the transceiver 48 were irradiated with the radiation X.

Figure 3:
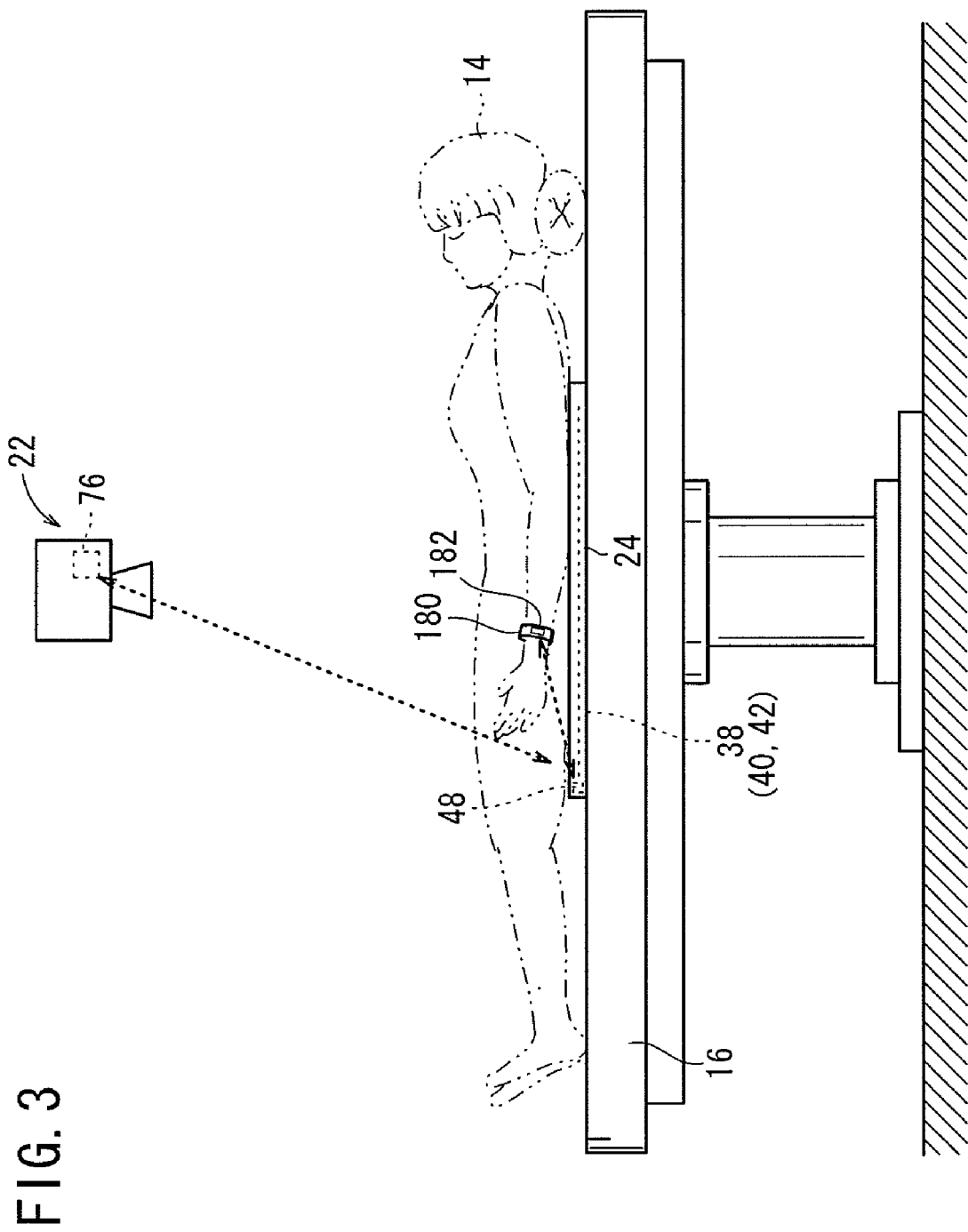
FIG. 3 is a side elevational view of an image capturing apparatus, the radiation detecting cassette, and a surgical table in the radiation image capturing system shown in FIG. 1.

FIG. 3 shows in side elevation the image capturing apparatus 22, the radiation detecting cassette 24, and the surgical table 16. The transceiver 48 of the radiation detecting cassette 24 can receive the subject ID information of the patient 14 which is stored in the RFID tag 182 from the RFID tag 182 by way of wireless communications. The transceiver 48 can also exchange signals with a transceiver (second wireless communication unit) 76 in the image capturing apparatus 22.

Figure 4:
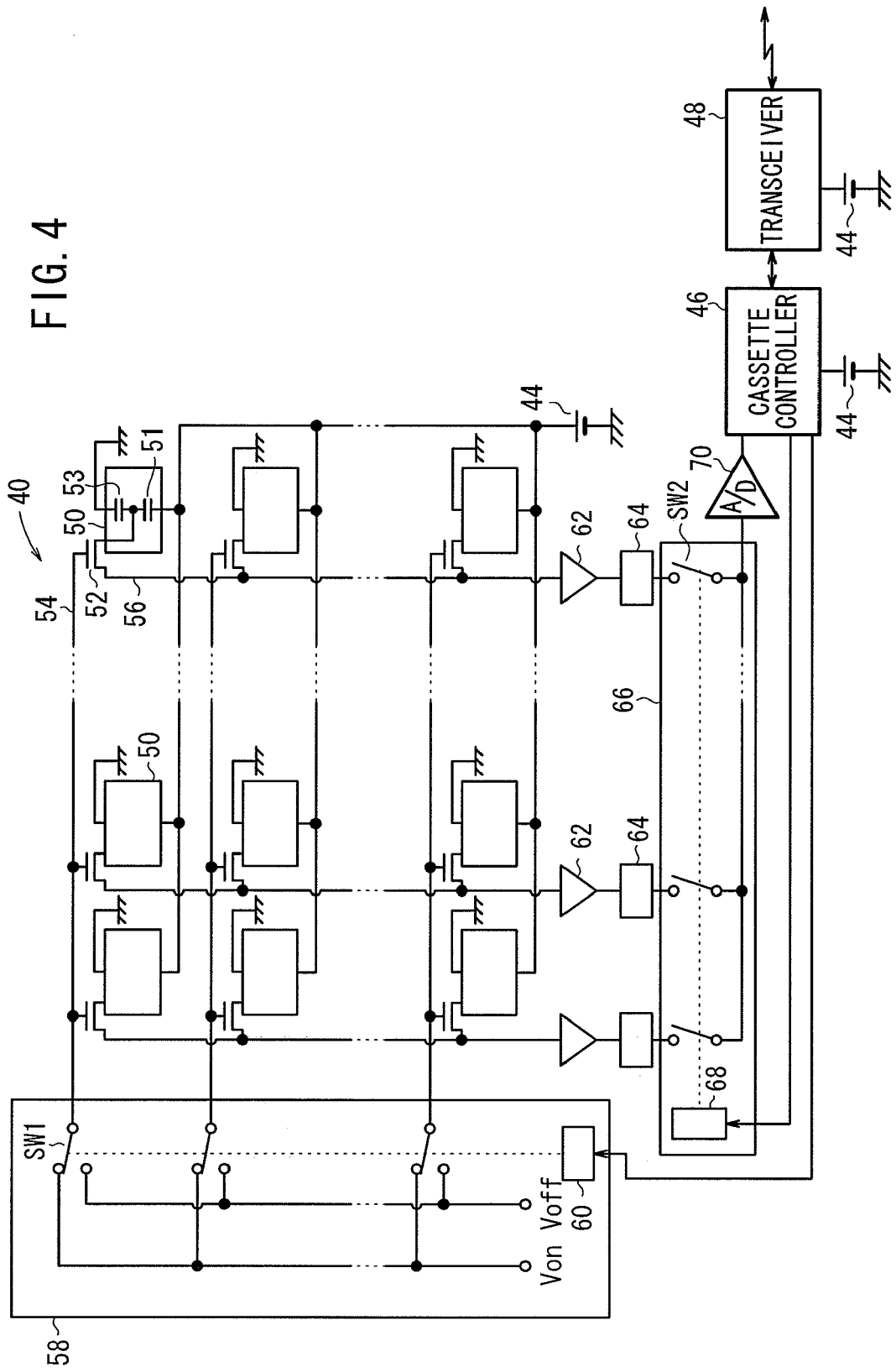
FIG. 4 is a block diagram of a circuit arrangement of a radiation detector of the radiation detecting cassette shown in FIG. 2.

FIG. 4 shows in block form a circuit arrangement of the radiation detector 40. As shown in FIG. 4, the radiation detector 40 comprises an array of thin-film transistors (TFTs) 52 arranged in rows and columns, a photoelectric conversion layer 51 made of a material such as amorphous selenium (a-Se) for generating electric charges upon detection of radiation X, the photoelectric conversion layer 51 being disposed over the array of TFTs 52, and an array of storage capacitors 53 connected to the photoelectric conversion layer 51. When radiation X is applied to the radiation detector 40, the photoelectric conversion layer 51 generates electric charges, and the storage capacitors 53 store the generated electric charges. Then, the TFTs 52 are turned on along each row at a time to read the electric charges from the storage capacitors 53 as an image signal. In FIG. 4, the photoelectric conversion layer 51 and one of the storage capacitors 53 are shown as making up a pixel 50, wherein the pixel 50 is connected to one of the TFTs 52. Details of the other pixels 50 are omitted from illustration. Since amorphous selenium tends to change its structure and lose its function at high temperatures, it needs to be used within a certain temperature range. Therefore, some means for cooling the radiation detector 40 should preferably be provided in the radiation detecting cassette 24.

The TFTs 52, which are connected to the respective pixels 50, are also connected to respective gate lines 54 extending in parallel to the rows, and to respective signal lines 56 extending in parallel to the columns. The gate lines 54 are connected to a line scanning driver 58, and the signal lines 56 are connected to a multiplexer 66 serving as a reading circuit. The gate lines 54 are supplied with control signals Von, Voff from the line scanning driver 58 for turning on and off the TFTs 52 along the rows. The line scanning driver 58 comprises a plurality of switches SW1 for switching between the gate lines 54 and an address decoder 60 for outputting a selection signal for selecting one of the switches SW1 at a time. The address decoder 60 is supplied with an address signal from the cassette controller 46.

The signal lines 56 are supplied with electric charges, which have been stored in the storage capacitors 53 of the pixels 50, through the TFTs 52 arranged in the columns. The electric charges supplied to the signal lines 56 are amplified by amplifiers 62 connected respectively to the signal lines 56. The amplifiers 62 are connected through respective sample and hold circuits 64 to the multiplexer 66. The multiplexer 66 comprises a plurality of switches SW2 for successively switching between the signal lines 56 and an address decoder 68 for outputting a selection signal for selecting one of the switches SW2 at a time. The address decoder 68 is supplied with an address signal from the cassette controller 46. The multiplexer 66 has an output terminal connected to an A/D converter 70. A radiation image signal generated by the multiplexer 66 based on the electric charges from the sample and hold circuits 64 is converted by the A/D converter 70 into a digital image signal representing radiation image information, which is supplied to the cassette controller 46.

Figure 5:
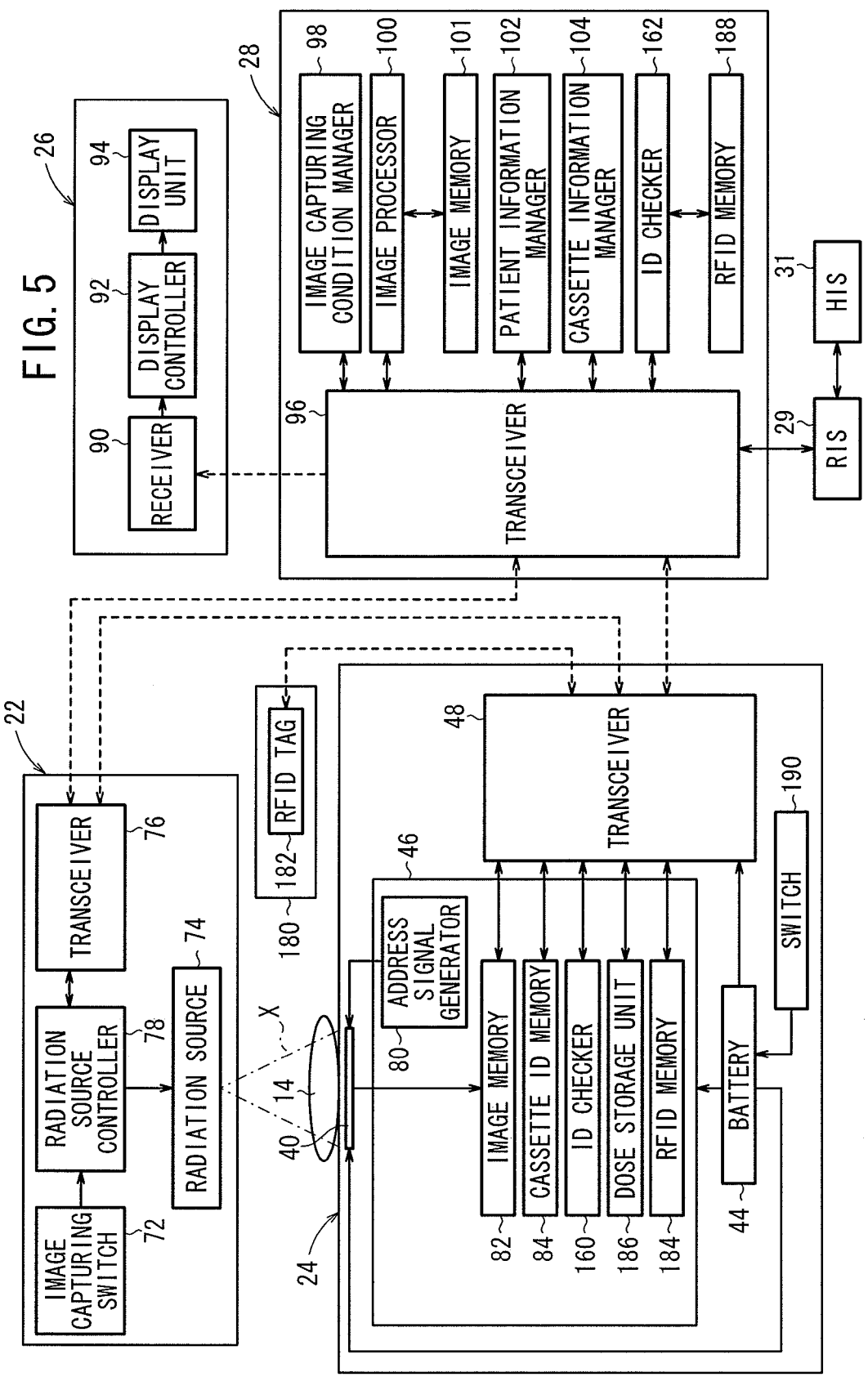
FIG. 5 is a block diagram of the radiation image capturing system shown in FIG. 1.

FIG. 5 shows in block form the radiation image capturing system 10 which comprises the image capturing apparatus 22, the radiation detecting cassette 24, the display device 26, the console 28, and the RFID tag 182. The console 28 is connected to a radiology information system (RIS) 29, which generally manages radiation image information handled by the radiological department of the hospital along with other information. The RIS 29 is connected to a hospital information system (HIS) 31, which generally manages medical information within the hospital.

The image capturing apparatus 22 comprises an image capturing switch 72, a radiation source 74, a transceiver 76, and a radiation source controller 78.

The transceiver 76 receives image capturing conditions from the console 28 by way of wireless communications and transmits an image capturing completion signal, etc. to the console 28 by way of wireless communications. The transceiver 76 is also capable of performing wireless communications with the transceiver 48 of the radiation detecting cassette 24, as described above.

The radiation source controller 78 controls the radiation source 74 based on an image capturing start signal supplied from the image capturing switch 72 and image capturing conditions supplied from the transceiver 76. The radiation source 74 outputs radiation X under the control of the radiation source controller 78.

The cassette controller 46 of the radiation detecting cassette 24 comprises an address signal generator 80, an image memory 82, a cassette ID memory 84, an ID checker 160, an RFID memory (ID storage unit) 184, and a dose storage unit (radiation dose storage unit) 186.

The address signal generator 80 supplies address signals to the address decoder 60 of the line scanning driver 58 and to the address decoder 68 of the multiplexer 66 of the radiation detector 40. The image memory 82 stores the radiation image information detected by the radiation detector 40. The cassette ID memory 84 stores cassette ID information for identifying the radiation detecting cassette 24. The transceiver 48 receives a transmission request signal from the console 28 by way of wireless communications and transmits the cassette ID information stored in the cassette ID memory 84 and the radiation image information stored in the image memory 82 to the console 28 by way of wireless communications.

The RFID memory 184 stores therein subject ID information of a plurality of patients 14. The dose storage unit 186 stores therein optimum radiation doses for the respective patients (subjects) 14 with respect to radiation X to be applied to the patients 14 when radiation images of the patients 14 are to be captured.

The ID checker 160 checks the subject ID information received by the transceiver 48 against the subject ID information stored in the RFID memory 184. If the subject ID information received by the transceiver 48 matches one of the subject ID information stored in the RFID memory 184, then the ID checker 160 reads a radiation dose corresponding to the matching subject ID information from the dose storage unit 186. The ID checker 160 regards the read radiation dose as an optimum radiation dose of the radiation X to be applied to the patient 14 having the matching subject ID information when a radiation image of the patient 14 is to be captured, associates the matching subject ID information with the read radiation dose, and transmits the matching subject ID information associated with the read radiation dose from the transceiver 48 to a transceiver (third wireless communication unit) 96 of the console 28 by way of wireless communications.

The display device 26 comprises a receiver 90 for receiving radiation image information from the console 28, a display controller 92 for controlling the display of the received radiation image information, and a display unit 94 for displaying radiation image information processed by the display controller 92.

The console 28 comprises a transceiver 96, an image capturing condition manager (control radiation dose storage unit) 98, an image processor (image processing unit) 100, an image memory 101, a patient information manager 102, a cassette information manager 104, an ID checker (control ID checker) 162, and an RFID memory (control ID storage unit) 188.

The transceiver 96 transmits and receives, by way of wireless communications, necessary information including radiation image information to and from the image capturing apparatus 22, the radiation detecting cassette 24, and the display device 26. The image capturing condition manager 98 manages image capturing conditions required for the image capturing apparatus 22 to capture radiation images. The image processor 100 processes radiation image information transmitted from the radiation detecting cassette 24. The image memory 101 stores radiation image information processed by the image processor 100. The patient information manager 102 manages patient information of the patient 14 whose images are to be captured. The cassette information manager 104 manages cassette ID information transmitted from the radiation detecting cassette 24.

The RFID memory 188 stores therein subject ID information of a plurality of patients 14, as with the RFID memory 184 in the radiation detecting cassette 24. The ID checker 162 checks the subject ID information received by the transceiver 96 against the subject ID information stored in the RFID memory 188. If the ID checker 162 judges that the subject ID information received by the transceiver 96 matches one of the subject ID information stored in the RFID memory 188, then based on the matching subject ID information and the radiation dose received by the transceiver 96, the image capturing condition manager 98 stores (registers) image capturing conditions depending on the radiation dose. If image capturing conditions with respect to the patient 14 having the matching subject ID information have already been registered in the image capturing condition manager 98, then the image capturing condition manager 98 updates the registered image capturing conditions according to the radiation dose.

The console 28 may be located outside of the operating room 12, assuming that it can transmit and receive signals to and from the image capturing apparatus 22, the radiation detecting cassette 24, and the display device 26 by way of wireless communications.

The image capturing conditions refer to condition for determining a tube voltage, a tube current, an irradiation time, etc., which are required to apply radiation X at an appropriate irradiation dose to an area of the patient 14 to be imaged. The image capturing conditions may include an area of the patient 14 to be imaged, an image capturing method, etc., for example. The patient information refers to information used for identifying the patient 14, such as the patient's name, gender, patient ID number, etc. Ordering information for ordering an image to be captured, including the image capturing conditions and the patient information can be set directly via the console 28 or can be supplied from an external source to the console 28 via the RIS 29. In the radiation image capturing system 10, upon transmission of the subject ID information from the RFID tag 182 to the radiation detecting cassette 24, image capturing conditions based on the radiation dose transmitted from the radiation detecting cassette 24 to the console 28 are registered (stored) in the image capturing condition manager 98.

The radiation image capturing system 10 according to the present embodiment is basically constructed as described above, and operations of the radiation image capturing system 10 will be described below.

The radiation image capturing system 10 is installed in the operating room 12 and used when a radiation image of the patient 14 is required by the surgeons 18 who are performing an operation on the patient 14. Before a radiation image of the patient 14 is captured, patient information of the patient 14 to be imaged is registered in the patient information manager 102 of the console 28. If a radiation dose, an area of the patient 14 to be imaged, and an image capturing method are already known, such conditions are registered as image capturing conditions in the image capturing condition manager 98. After the above preparatory process is finished, the surgeons 18 perform an operation on the patient 14.

For capturing a radiation image of the patient 14 during an operation, one of the surgeons 18 or a radiological technician places the radiation detecting cassette 24 between the patient 14 and the surgical table 16, with the irradiated surface 36 facing the image capturing apparatus 22. Then, after having moved the image capturing apparatus 22 to a position confronting the radiation detecting cassette 24, one of the surgeons 18 or the radiological technician turns on the image capturing switch 72.

Figure 6:
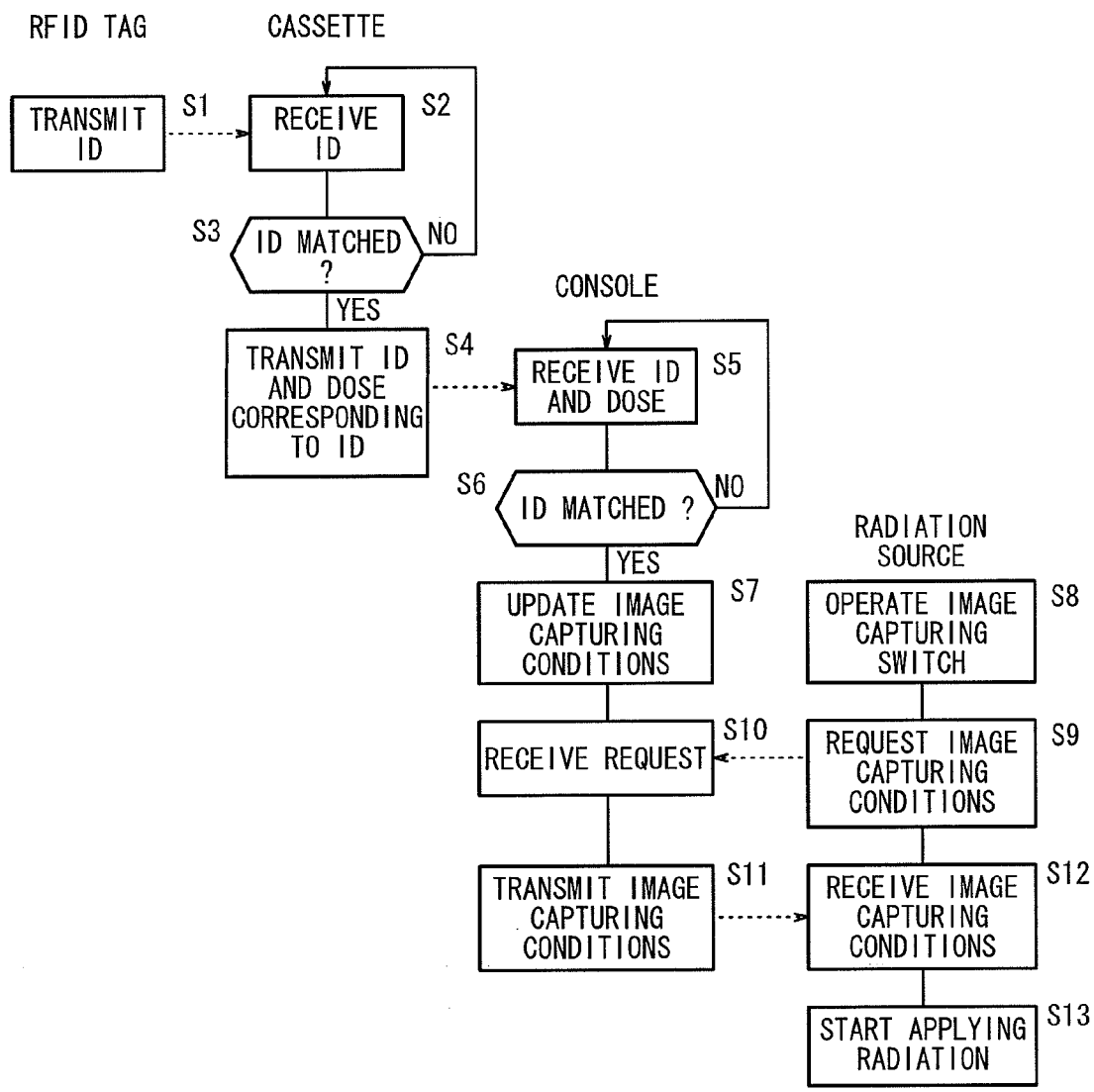
FIG. 6 is a flowchart of an operation sequence of the radiation image capturing system from the transmission of subject ID information from an RFID tag to the application of a radiation

FIG. 6 is a flowchart of an operation sequence of the radiation image capturing system 10 from the transmission of subject ID information from the RFID tag 182 to the radiation detecting cassette 24 in step S1 to the application of radiation X to the patient 14 in step S13.

In step S1, when one of the surgeons 18 or the radiological technician places the radiation detecting cassette 24 at a predetermined position between the patient 14 and the surgical table 16 with the irradiated surface 36 facing the image capturing apparatus 22, the RFID tag 182 sends its own subject ID information. When the transceiver 48 of the radiation detecting cassette 24 receives the subject ID information from the RFID tag 182 in step S2, the ID checker 160 checks the subject ID information received by the transceiver 48 against the subject ID information stored in the RFID memory 184, and determines whether the subject ID information received by the transceiver 48 matches one of the subject ID information stored in the RFID memory 184 in step S3.

If the ID checker 160 judges that the subject ID information received by the transceiver 48 matches one of the subject ID information stored in the RFID memory 184 in step S3, then the ID checker 160 reads the radiation dose corresponding to the matching subject ID information from the dose storage unit 186, associates the matching subject ID information with the read radiation dose, and transmits the matching subject ID information associated with the read radiation dose from the transceiver 48 to the transceiver 96 of the console 28 by way of wireless communications in step S4.

If the ID checker 160 judges that the subject ID information received by the transceiver 48 does not match any one of the subject ID information stored in the RFID memory 184 in step S3, then the radiation detecting cassette 24 does not perform the processing in step S4, but perform the processing in step S2 again.

When the transceiver 96 of the console 28 receives the associated subject ID information and the radiation dose in step S5, the ID checker 162 checks the subject ID information received by the transceiver 96 against the subject ID information stored in the RFID memory 188, and determines whether the subject ID information received by the transceiver 96 matches one of the subject ID information stored in the RFID memory 188 in step S6.

If the ID checker 162 judges that the subject ID information received by the transceiver 96 matches one of the subject ID information stored in the RFID memory 188 in step S6, then the image capturing condition manager 98 stores (updates) image capturing conditions based on the radiation dose which has been received together with the matching subject ID information by the transceiver 96 in step S7.

If the ID checker 162 judges that the subject ID information received by the transceiver 96 does not match any one of the subject ID information stored in the RFID memory 188 in step S6, then the console 28 does not perform the processing in step S7, but perform the processing in step S5 again.

When one of the surgeons 18 or the radiological technician turns on the image capturing switch 72 (see FIG. 5) in step S8, the radiation source controller 78 of the image capturing apparatus 22 requests the console 28 to transmit the image capturing conditions via the transceivers 76, 96 in step S9.

The console 28 receives the request in step S10, and transmits the image capturing conditions about the area of the patient 14 to be imaged, which are registered in the image capturing condition manager 98, to the image capturing apparatus 22 via the transceivers 96, 76 in step S11. When the radiation source controller 78 receives the image capturing conditions in step S12, it controls the radiation source 74 in order to apply radiation X at a given radiation dose, i.e., a radiation dose according to the subject ID information, to the patient 14 according to the image capturing conditions in step S13.

Subsequently to step S13, radiation X which has passed through the patient 14 is applied to the grid 38, which removes scattered rays of the radiation X. Then, the radiation X is applied to the radiation detector 40, and converted into electric signals by the photoelectric conversion layer 51 of each of the pixels 50 of the radiation detector 40. The electric signals are stored as electric charges in the storage capacitors 53 (see FIG. 4). The stored electric charges, which represent radiation image information of the patient 14, are read from the storage capacitors 53 according to address signals which are supplied from the address signal generator 80 of the cassette controller 46 to the line scanning driver 58 and to the multiplexer 66.

Specifically, in response to the address signal supplied from the address signal generator 80, the address decoder 60 of the line scanning driver 58 outputs a selection signal so as to select one of the switches SW1, which supplies the control signal Von to the gates of the TFTs 52 connected to the gate line 54 corresponding to the selected switch SW1. In response to the address signal supplied from the address signal generator 80, the address decoder 68 of the multiplexer 66 outputs a selection signal, which operates to successively turn on the switches SW2 so as to switch between the signal lines 56, for thereby reading the electric charges stored in the storage capacitors 53 of the pixels 50 connected to the gate line 54 that has been selected by the line scanning driver 58, through the signal lines 56.

The electric charges read from the storage capacitors 53 of the pixels 50, which are connected to the selected gate line 54, are amplified by respective amplifiers 62, sampled by the sample and hold circuits 64, and supplied to the multiplexer 66. Based on the supplied electric charges, the multiplexer 66 generates and supplies a radiation image signal to the A/D converter 70, which converts the radiation image signal into a digital signal. The digital signal which represents the radiation image information is stored in the image memory 82 of the cassette controller 46.

Similarly, the address decoder 60 of the line scanning driver 58 successively turns on the switches SW1 to switch between the gate lines 54 according to the address signal supplied from the address signal generator 80. The electric charges stored in the storage capacitors 53 of the pixels 50, which are connected to the successively selected gate lines 54, are read through the signal lines 56, and processed by the multiplexer 66 and the A/D converter 70 into digital signals, which are stored in the image memory 82 of the cassette controller 46.

The radiation image information represented by the digital signals stored in the image memory 82 is transmitted through the transceiver 48 to the console 28 by way of wireless communications.

The radiation image information transmitted to the console 28 is received by the transceiver 96, processed by the image processor 100, and then stored in the image memory 101 in association with the patient information of the patient 14 registered in the patient information manager 102.

The radiation image information processed by the image processor 100 is transmitted from the transceiver 96 to the display device 26. In the display device 26, the receiver 90 receives the radiation image information, and the display controller 92 controls the display unit 94 so as to display a radiation image based on the radiation image information. The surgeons 18 perform an operation on the patient 14 while visually confirming the radiation image displayed on the display unit 94.

In the radiation image capturing system 10 according to the present embodiment, the transceiver 48 of the radiation detecting cassette 24 receives the subject ID information of the patient 14 from the RFID tag 182 by way of wireless communications, and the ID checker 160 checks the subject ID information received by the transceiver 48 against the subject ID information stored in the RFID memory 184. If the subject ID information received by the transceiver 48 matches one of the subject ID information stored in the RFID memory 184, then the ID checker 160 associates the matching subject ID information with the radiation dose that is stored in the dose storage unit 186 and corresponds to the matching subject ID information.

It is thus possible to manage a radiation dose for each patient 14, and to adjust the radiation dose of the radiation X for each patient 14 at the time a radiation image of each patient 14 is to be captured.

The transceiver 48 transmits the associated subject ID information and the radiation dose to the transceiver 96 of the console 28 by way of wireless communications. The ID checker 162 of the console 28 checks the subject ID information received by the transceiver 96 against the subject ID information stored in the RFID memory 188. If the subject ID information received by the transceiver 96 matches one of the subject ID information stored in the RFID memory 188, then the image capturing condition manager 98 stores (updates) image capturing conditions based on the radiation dose which has been received together with the matching subject ID information by the transceiver 96. The console 28 is thus capable of easily and accurately managing the radiation dose (image capturing conditions) for the patient 14 having the matching subject ID information.

When the console 28 receives a request for the transmission of image capturing conditions of the patient 14 from the image capturing apparatus 22, the console 28 transmits the image capturing conditions stored in the image capturing condition manager 98 to the image capturing apparatus 22. Therefore, the patient 14 can be irradiated with the radiation X at a radiation dose optimum for the patient 14, when a radiation image of the patient 14 is to be captured.

Furthermore, signals are transmitted and received by way of the UWB wireless communications between the radiation detecting cassette 24 and the console 28, between the radiation detecting cassette 24 and the image capturing apparatus 22, between the image capturing apparatus 22 and the console 28, between the console 28 and the display device 26, and between the radiation detecting cassette 24 and the RFID tag 182. In other words, since cables for transmitting and receiving signals are not connected between the image capturing apparatus 22, the radiation detecting cassette 24, the display device 26, the console 28, and the RFID tag 182, such cables are not placed on the floor of the operating room 12 where they would become obstacles to the operation performed by the surgeons 18, the radiological technician, or to other staff members present in the operating room 12. The surgeons 18, the radiological technician, and other staff members in the operating room 12 can perform work more efficiently. The UWB wireless communications also make it possible to reduce power consumption, increase fading resistance, and increase communication rates, compared with other wireless communications.

In the radiation image capturing system 10 according to the illustrated embodiment, the subject ID information and the radiation dose are transmitted from the transceiver 48 to the transceiver 96 by way of wireless communications. However, the subject ID information and the radiation dose may be transmitted (transferred) from the transceiver 48 via the transceiver 76 to the transceiver 96 by way of wireless communications.

Also, in the radiation image capturing system 10 according to the present invention, as described above, if the subject ID information received by the transceiver 48 matches one of the subject ID information stored in the RFID memory 184, then the ID checker 160 associates the matching subject ID information with the radiation dose which is stored in the dose storage unit 186. Instead of the above processes, the following processes (1) or (2) may be performed to obtain the same effects as in the aforementioned embodiments.

(1) The image capturing condition manager 98 stores, in advance, image capturing conditions for each patient 14 (each subject), which include a radiation dose for each patient 14 having subject ID information. The transceiver 48 transmits the received subject ID information to the transceiver 96. The ID checker 162 checks the subject ID information received by the transceiver 96 against the subject ID information stored in the RFID memory 188. If the subject ID information received by the transceiver 96 matches one of the subject ID information stored in the RFID memory 188, then the ID checker 162 associates the matching subject ID information with the radiation dose (image capturing condition) stored in the image capturing condition manager 98 and corresponding to the subject ID information.

(2) The ID checker 160 checks the subject ID information received by the transceiver 48 against the subject ID information stored in the RFID memory 184. If the subject ID information received by the transceiver 48 matches one of the subject ID information stored in the RFID memory 184, then the transceiver 48 transmits the matching subject ID information to the transceiver 96 by way of wireless communications, and the matching subject ID information is associated with the radiation dose (image capturing condition) stored in the image capturing condition manager 98 and corresponding to the subject ID information.

The radiation image capturing system 10 according to the illustrated embodiment captures a radiation image of the patient 14 when one of the surgeons 18 or the radiological technician turns on the image capturing switch 72. However, the radiation image capturing system 10 may also be configured to capture a radiation image of the patient 14 when one of the surgeons 18 or the radiological technician operates the console 28.

In the radiation image capturing system 10 according to the illustrated embodiment, the radiation detector 40 housed in the radiation detecting cassette 24 directly converts the dose of the applied radiation X into an electric signal via the photoelectric conversion layer 51. However, the radiation image capturing system 10 may employ a radiation detector including a scintillator for converting the applied radiation X into visible light together with a solid-state detecting device made up of amorphous silicon (a-Si) or the like for converting the visible light into electric signals (see Japanese Patent No. 3494683).

Alternatively, the radiation image capturing system 10 may employ a light-conversion radiation detector for acquiring radiation image information. The light-conversion radiation detector operates as follows: When radiation is applied to a matrix of solid-state detecting devices, the solid-state detecting devices store an electrostatic latent image depending on the dose of the applied radiation. For reading the stored electrostatic latent image, reading light is applied to the solid-state detecting devices, thereby causing the solid-state detecting devices to generate an electric current representing the radiation image information. When erasing light is applied to the radiation detector, radiation image information representing a residual electrostatic latent image is erased from the radiation detector, which can thus be reused (see Japanese Laid-Open Patent Publication No. 2000-105297).

When the radiation detecting cassette 24 is used in the operating room 12 or the like, the radiation detecting cassette 24 may be subjected to adhesion of blood, contamination, etc. However, when the radiation detecting cassette 24 is designed to have a waterproof and hermetically-sealed structure, and is sterilized and cleaned as necessary, one radiation detecting cassette 24 can be used repeatedly.

The radiation detecting cassette 24 is not limited to use in the operating room 12, and may be used for a medical examination and a round in the hospital.

Also, the radiation detecting cassette 24 may communicate with external devices via optical wireless communication using infrared light or the like, instead of general wireless communication using radio wave.

Figure 7:
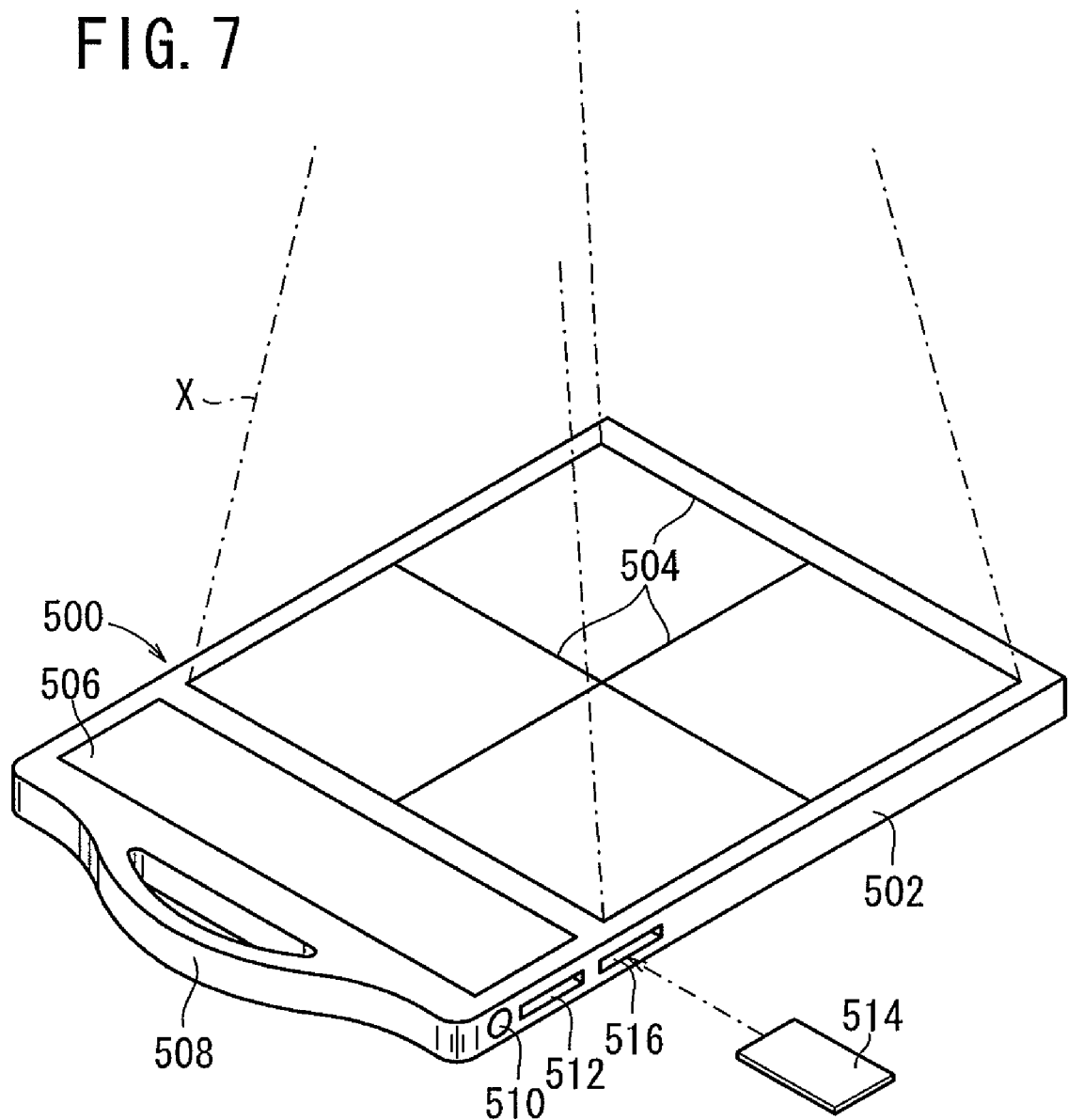
FIG. 7 is a perspective view showing a radiation detecting cassette in the radiation image capturing system according to another embodiment of the present invention.

Preferably, the radiation detecting cassette 500 may be constructed as shown in FIG. 7.

Specifically, the radiation detecting cassette 500 includes a guiding line 504 drawn on the radiation-irradiated surface of a casing 502, the guiding line 504 serving as a reference for setting a captured area and a captured position. Using the guiding line 504, a subject (patient 14) can be positioned with respect to the radiation detecting cassette 500, and an area irradiated with the radiation X can be set, thereby recording radiation image information on an appropriate captured area.

The radiation detecting cassette 500 is provided with a display section 506 on an area thereof other than the captured area, for displaying various information about the radiation detecting cassette 500. The information which is displayed on the display section 506, includes ID information of a patient 14 whose radiation image information is to be recorded on the radiation detecting cassette 500, the number of times the radiation detecting cassette 500 has been used, an accumulated exposed radiation dose, a charging state (remaining battery level) of a battery 44 in the radiation detecting cassette 500, image capturing conditions of radiation image information, and a positioning image of the patient 14 with respect to the radiation detecting cassette 500. In this case, a radiological technician confirms a patient 14 based on the ID information displayed on the display section 506, for example, and also previously confirms that the radiation detecting cassette 500 is placed in a usable state. Then, the technician positions a desired captured area of the patient 14 with respect to the radiation detecting cassette 500 based on the displayed positioning image, thereby capturing appropriate radiation image information.

Also, the radiation detecting cassette 500 is provided with a handgrip 508, whereby it is easier to handle and carry the radiation detecting cassette 500.

Preferably, the radiation detecting cassette 500 may have, on a side thereof, an input terminal 510 for an AC adapter, a USB (Universal Serial Bus) terminal 512, and a card slot 516 for inserting a memory card 514.

When the charging function of the battery 44 in the radiation detecting cassette 500 becomes deteriorated, or when there is not enough time to fully charge the battery 44, the input terminal 510 is connected to the AC adapter to externally supply the radiation detecting cassette 500 with electric power, thereby enabling the radiation detecting cassette 500 to be used immediately.

The USB terminal 512 or the card slot 516 may be used when the radiation detecting cassette 500 cannot transmit and receive information to and from external devices such as the console 28 via wireless communication. Specifically, by connecting a cable to the USB terminal 512, the radiation detecting cassette 500 can transmit and receive information to and from the external devices via wire communication. Alternatively, the memory card 514 is inserted into the card slot 516, and necessary information is recorded on the memory card 514. After that, the memory card 514 is removed from the card slot 516, and the memory card 514 is inserted into the external device, thereby enabling information to be transferred.

Figure 8:
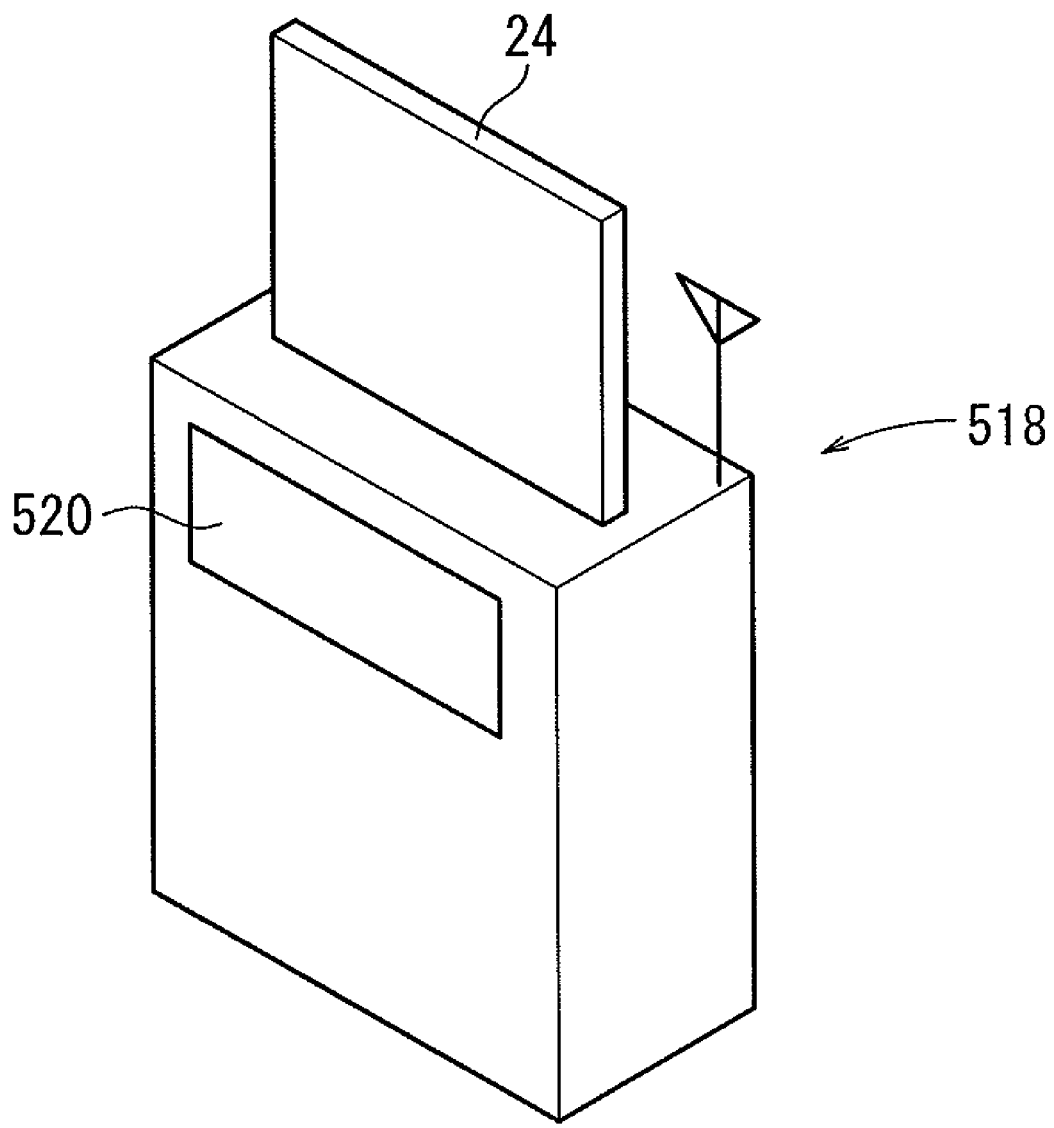
FIG. 8 is a perspective view showing a cradle which charges the radiation detecting cassette.

Preferably, a cradle 518 may be disposed in the operating room 12 or at a desired place in the hospital, into which the radiation detecting cassette 24 is inserted to charge the internal battery 44, as shown in FIG. 8. In this case, in addition to charging the battery 44, the cradle 518 may transmit and receive necessary information to and from external devices such as HIS 31, RIS 29, the console 28, etc. by way of wireless or wire communications of the cradle 518. The information may include radiation image information which is recorded on the radiation detecting cassette 24 inserted into the cradle 518.

Also, the cradle 518 may be provided with a display section 520. The display section 520 may display necessary information including a charging state of the inserted radiation detecting cassette 24 and radiation image information acquired from the radiation detecting cassette 24.

Further, a plurality of cradles 518 may be connected to a network. In this case, information about charging states of radiation detecting cassettes 24 inserted in respective cradles 518 can be collected through the network, and the radiation detecting cassette 24 in a usable state can be located.

Although certain preferred embodiments of the present invention have been shown and described in detail, it should be understood that various changes and modifications may be made to the embodiments without departing from the scope of the invention as set forth in the appended claims.

What is claimed is:

1. A radiation image capturing system comprising:
   a radiation source for outputting a radiation;
   a radiation detecting cassette housing therein a radiation conversion panel for detecting said radiation that has passed through a subject and converting the detected radiation into radiation image information;
   an RFID tag mounted on the subject and storing subject ID information for identifying the subject;
   an ID storage unit for storing a plurality of pieces of subject ID information;
   an ID checker;
   a radiation dose storage unit for storing radiation doses corresponding to the subject ID information; and
   said radiation detecting cassette comprising a first wireless communication unit;
   wherein said first wireless communication unit receives the subject ID information from said RFID tag by way of wireless communications;
   wherein said ID checker checks the subject ID information received by said first wireless communication unit against the subject ID information stored in said ID storage unit, and if the subject ID information received by said first wireless communication unit matches one of the subject ID information stored in said ID storage unit, said ID checker associates the matching subject ID information with a radiation dose which is stored in said radiation dose storage unit and which corresponds to the matching subject ID information;
   further comprising a controller for controlling said image capturing apparatus and said radiation detecting cassette, said controller having a third wireless communication unit;
   wherein when said ID storage unit, said ID checker, and said radiation dose storage unit are disposed in said radiation detecting cassette, said first wireless communication unit transmits the associated subject ID information and the radiation dose to said third wireless communication unit by way of wireless communications;
   wherein said ID storage unit, said ID checker, and said radiation dose storage unit are disposed in said radiation detecting cassette, and a control ID storage unit for storing a plurality of pieces of subject ID information, a control ID checker, and a control radiation dose storage unit are disposed in said controller;
   wherein said control ID checker checks the subject ID information received by said third wireless communication unit against the subject ID information stored in said control ID storage unit, and if the subject ID information received by said third wireless communication unit matches one of the subject ID information stored in said control ID storage unit, said control ID checker stores the radiation dose received by said third wireless communication unit into said control radiation dose storage unit; and further comprising:
   an image capturing apparatus having a second wireless communication unit for performing wireless communications with said first wireless communication unit, said radiation source and a radiation source controller being disposed in said image capturing apparatus.

2. A radiation image capturing system according to claim 1, wherein when said ID storage unit, said ID checker, and said radiation dose storage unit are disposed in said controller, said first wireless communication unit transmits the subject ID information received from said RFID tag, to said third wireless communication unit by way of wireless communications, and said ID checker checks the subject ID information received by said third wireless communication unit against the subject ID information stored in said ID storage unit.

3. A radiation image capturing system according to claim 1, wherein when said ID storage unit and said ID checker are disposed in said radiation detecting cassette, and said radiation dose storage unit is disposed in said controller, said ID checker checks the received subject ID information against the subject ID information stored in said ID storage unit, and if the received subject ID information matches one of the subject ID information stored in said ID storage unit, said first wireless communication unit transmits the matching subject ID information to said third wireless communication unit by way of wireless communications, and the matching subject ID information transmitted from said first wireless communication unit is associated with a radiation dose which is stored in said radiation dose storage unit and which corresponds to the matching subject ID information.

4. A radiation image capturing system according to claim 1, wherein said first, second, and third wireless communication units are capable of performing UWB wireless communications with each other.

5. A radiation image capturing system according to claim 1, wherein when said controller receives a request for transmitting image capturing conditions of the subject from said image capturing apparatus, said controller transmits, to said image capturing apparatus, the image capturing conditions including the radiation dose stored in said control radiation dose storage unit.

6. A radiation image capturing system according to claim 1, wherein said first wireless communication unit transmits the radiation image information converted by said radiation conversion panel, to said third wireless communication unit by way of wireless communications.

7. A radiation image capturing system according to claim 1, further comprising:
   a controller for controlling said image capturing apparatus and said radiation detecting cassette;
   wherein said first wireless communication unit transmits the associated subject ID information and the radiation dose to said second wireless communication unit by way of wireless communications; and
   said image capturing apparatus transfers, to said controller, the associated subject ID information and the radiation dose received by said second wireless communication unit.

8. A radiation image capturing system according to claim 7, wherein said ID storage unit, said ID checker, and said radiation dose storage unit are disposed in said radiation detecting cassette, and a control ID storage unit for storing a plurality of pieces of subject ID information, a control ID checker, and a control radiation dose storage unit are disposed in said controller; and
   wherein said control ID checker checks the subject ID information transferred from said image capturing apparatus to said controller against the subject ID information stored in said control ID storage unit, and if the subject ID information transferred from said image capturing apparatus to said controller matches one of the subject ID information stored in said control ID storage unit, said control ID checker stores the radiation dose transferred to said controller, into said control radiation dose storage unit.

9. A radiation image capturing system according to claim 1, wherein said first wireless communication unit and said RFID tag are capable of performing UWB wireless communications with each other.

10. A radiation image capturing system according to claim 1, wherein said radiation conversion panel acquires said radiation image information by directly converting said radiation into an electric signal.

11. A radiation image capturing system according to claim 1, further comprising:
a substantially rectangular casing housing therein said radiation conversion panel, said ID storage unit, said ID checker, said radiation dose storage unit, and said first wireless communication unit, said casing being made of a material permeable to said radiation.

12. A radiation image capturing system according to claim 1, further comprising:
a display device for displaying a radiation image based on said radiation image information;
wherein said controller and said display device are capable of performing UWB wireless communications with each other.

13. A radiation image capturing system according to claim 1, further comprising:
a wrist band having said RFID tag, said wrist band being mounted on a wrist of said patient.

14. A radiation image capturing system according to claim 1, wherein the ID checker associates matching subject ID information with the radiation dose stored in the radiation dose storage unit prior to capturing of an image by the image capturing apparatus.

* * * * *